United States Patent
Grimme et al.

(10) Patent No.: US 7,857,847 B2
(45) Date of Patent: Dec. 28, 2010

(54) ONE-PIECE HEART PROSTHESIS IMPLANTABLE IN AN ANATOMICAL POSITION

(75) Inventors: Marc Grimme, Paris (FR); Maurice Koechler, Orsay (FR); Jean-Marc Parquet, Domont (FR); Alain Carpentier, Paris (FR)

(73) Assignee: Carmat, Paris (FR)

( * ) Notice: Subject to any disclaimer, the term of this patent is extended or adjusted under 35 U.S.C. 154(b) by 11 days.

(21) Appl. No.: 12/304,443

(22) PCT Filed: Jun. 11, 2007

(86) PCT No.: PCT/FR2007/000962

§ 371 (c)(1),
(2), (4) Date: Dec. 11, 2008

(87) PCT Pub. No.: WO2007/144497

PCT Pub. Date: Dec. 21, 2007

(65) Prior Publication Data

US 2009/0192607 A1  Jul. 30, 2009

(30) Foreign Application Priority Data

Jun. 15, 2006 (FR) .................................. 06 05333

(51) Int. Cl.
*A61M 1/10* (2006.01)
(52) U.S. Cl. ..................................... 623/3.17; 623/3.16
(58) Field of Classification Search .......... 623/3.2–3.28
See application file for complete search history.

(56) References Cited

U.S. PATENT DOCUMENTS

| 4,058,857 | A | * | 11/1977 | Runge et al. | ................ 623/3.17 |
| 4,750,903 | A | * | 6/1988 | Cheng | ........................ 623/3.25 |
| 5,135,539 | A | | 8/1992 | Carpentier | |
| 5,976,184 | A | * | 11/1999 | Buecherl et al. | ........... 623/3.18 |
| 6,342,072 | B1 | * | 1/2002 | Wartelle et al. | ............... 623/3.2 |

FOREIGN PATENT DOCUMENTS

FR  2 585 250  1/1987

OTHER PUBLICATIONS

International Search Report dated Oct. 31, 2007 w/ English translation.
Written Opinion of the International Searching Authority with English translation.
A. Shah, "Intraoperative Determination of Mediastinal Constraints for a Total Artificial Heart," Asaio Transactions, Harper and Row Publishers, Hagerstown, MD,US, vol. 37, No. 2, Apr. 1, 1991, pp. 76-79, XP000215535.

* cited by examiner

*Primary Examiner*—Suzette J Gherbi
(74) *Attorney, Agent, or Firm*—Dickinson Wright PLLC

(57) ABSTRACT

One-piece heart prosthesis implantable in an anatomical position. According to the invention, the artificial left and right ventricles (2, 8) have general directions (14, 15) arranged in an asymmetrical V shape, such that said ventricles approach each other as they move away from the means (6, 12) of connection to the natural left and right auricles, and the individual hydraulic actuators (7, 13), associated respectively with said artificial left and light ventricles (2, 8), are arranged near each other, in proximity to said artificial left ventricle (2).

13 Claims, 7 Drawing Sheets

ONE-PIECE HEART PROSTHESIS IMPLANTABLE IN AN ANATOMICAL POSITION

TECHNICAL FIELD OF THE INVENTION

The present invention relates to a one-piece heart prosthesis implantable in an anatomical position.

BACKGROUND OF THE INVENTION

Document U.S. Pat. No. 5,135,539 has already disclosed a heart prosthesis which is implantable in the pericardial cavity of a patient and which is able to replace the natural left and right ventricles of said patient after their removal. This heart prosthesis comprises a rigid body in which artificial left and right ventricles are arranged, each of these artificial ventricles comprising a flexible membrane:

which is able to beat under the action of a hydraulic fluid, and which is arranged in a cavity divided in a leaktight manner by said membrane into two chambers, one of which is intended for the circulation of the blood, and the other of which is filled with said hydraulic fluid.

Furthermore, the hydraulic fluid chamber of each of said artificial ventricles is connected to an individual hydraulic actuator, which itself communicates with a leaktight pouch surrounding the prosthesis and containing said hydraulic fluid. The blood chamber of the artificial left ventricle comprises an orifice of connection to the natural left auricle and means of connection to the aorta, while the blood chamber of the artificial right ventricle comprises an orifice of connection to the natural right auricle and means of connection to the pulmonary artery, the axes of said orifices of connection to the natural auricles being co-planar, and said artificial ventricles having, parallel to the plane of said axes of said orifices, directions arranged in a V-shape, such that said ventricles approach each other as they move away from said orifices of connection to the natural auricles.

In the embodiment in document U.S. Pat. No. 5,135,539, the artificial ventricles of said heart prosthesis are arranged in a strictly symmetrical fashion with respect to a median plane, with their opposing individual hydraulic actuators protruding laterally from said rigid body. This has the result that the overall size of said prosthesis is not optimal and that difficulties may arise during implantation in the thoracic and pericardial cavity of many patients.

SUMMARY OF THE INVENTION

The object of the present invention is to overcome this disadvantage. To this end, according to the invention, the heart prosthesis of the type cited above is characterized:

in that said axes of said orifices of connection to the natural auricles are at least approximately parallel;

in that said V-shaped arrangement of the artificial left and right ventricles is asymmetrical with respect to said axes, the angle formed between the general direction of the artificial right ventricle and the axis of said orifice of connection to the natural right auricle being greater than the angle formed between the general direction of the artificial left ventricle and the axis of said orifice of connection to the natural left auricle; and in that said individual hydraulic actuators, associated respectively with said artificial left and right ventricles, are arranged near each other, on the side of said artificial left ventricle.

Thus, by virtue of the present invention, the offset positioning of said individual hydraulic actuators and the asymmetrical V-shaped arrangement of said artificial ventricles make it possible to position the blood compartments opposite the corresponding natural auricles while at the same time giving said prosthesis a shape and a volume close to the anatomical shape and volume of the pericardial cavity, thereby allowing said prosthesis to be lodged in said cavity.

In the case where the prosthesis according to the present invention is intended for an adult, the distance between said parallel axes can be at least approximately equal to 45 mm.

As regards the individual hydraulic actuators, they can be arranged anywhere to the side of the artificial left ventricle, in particular in proximity to the tip of said V.

In order to further enhance the beneficial effects afforded by the invention, it is advantageous that the dimensions of said artificial ventricles, parallel to said general directions, are smaller than the dimensions of said ventricles perpendicular to said general directions, and that the general directions of the two artificial ventricles form between them an angle at least approximately equal to 80°.

Thus, more space is gained parallel to the antero-posterior axis of the thorax.

In the usual case where each of said artificial ventricles has the shape of two domes arranged opposite with respect to a common base, it is then advantageous that said common base has the shape of an ellipse, of which the minor axis is at least substantially parallel to said corresponding general direction.

In the particular case where the prosthesis is intended for an adult and where each artificial ventricle must have a volume of the order of 70 cm$^3$, the lengths of the minor axis and of the major axis of said elliptic base are preferably at least approximately equal to 64 mm and 87 mm, respectively. The distance between the summits of the two domes of a ventricle is then at least approximately equal to 30 mm.

In a general manner, the asymmetrical and overlapping arrangement of the ventricles and of the hydraulic actuators, which constitutes one of the original features of said heart prosthesis, makes it possible to reduce its size as far as possible, thereby making it easier to lodge the prosthesis in the pericardial cavity.

In the illustrative embodiment above, in which said general directions of the two artificial ventricles form between them an angle at least approximately equal to 80°, it is advantageous that the angle formed between the general direction of the artificial right ventricle and the axis of said orifice of connection to the natural right auricle is at least approximately equal to 50°, and that the angle formed between the general direction of the artificial left ventricle and the axis of said orifice of connection to the natural left auricle is at least approximately equal to 30°.

By virtue of the arrangement of said individual hydraulic actuators in proximity to the artificial left ventricle, the individual hydraulic actuator associated with the artificial right ventricle is at a distance from the latter. Thus, according to the present invention; a conduit is provided, outside said rigid body, in order to connect said artificial right ventricle to the associated individual hydraulic actuator.

In a known manner, each artificial ventricle can be composed, on the one hand, of a dome-shaped recess formed in said rigid body such that the edge of this recess forms said common base, and, on the other hand, of a cover, also dome-shaped, which can be connected to said common base by fixing the corresponding membrane to the latter. In this arrangement, each individual hydraulic actuator communicates with the corresponding ventricle via the associated cover. Thus, in this case, the hydraulic actuator associated with the artificial right ventricle is connected to the cover of the latter via said conduit outside said rigid body.

Moreover, said heart prosthesis according to the present invention can comprise:

a flexible pouch surrounding, amply and sealingly, at least part of said rigid body by enclosing said hydraulic actuators and the electronics for control, signal processing and communication, said pouch being filled with said hydraulic fluid and serving as a container for the hydraulic circuit of said actuators. Said pouch, being very wide, is driven by beats of low amplitude, which thus avoids the need for a compliance chamber remote from the prosthesis. Moreover, by surrounding the actuators and the control electronics, said pouch protects these and facilitates heat exchange between actuators, ventricular chambers and adjacent tissues; and a surrounding openworked and rigid wall which is integral with said rigid body and which is arranged between the latter and said flexible pouch, in such a way that said flexible pouch is not aspirated by the actuators during filling of the ventricles.

A clearance volume for said flexible pouch is advantageously formed between it and said openworked rigid wall. Such a clearance volume can be at least approximately equal to twice the volume of the hydraulic fluid chamber of one of said artificial ventricles and is distributed across the full surface of the rigid wall.

BRIEF DESCRIPTION OF THE DRAWINGS

From the figures in the attached drawing, it will be clearly understood how the invention can be realized. In these figures, identical reference signs designate similar elements.

DETAILED DESCRIPTION OF THE INVENTION

Figure 1:
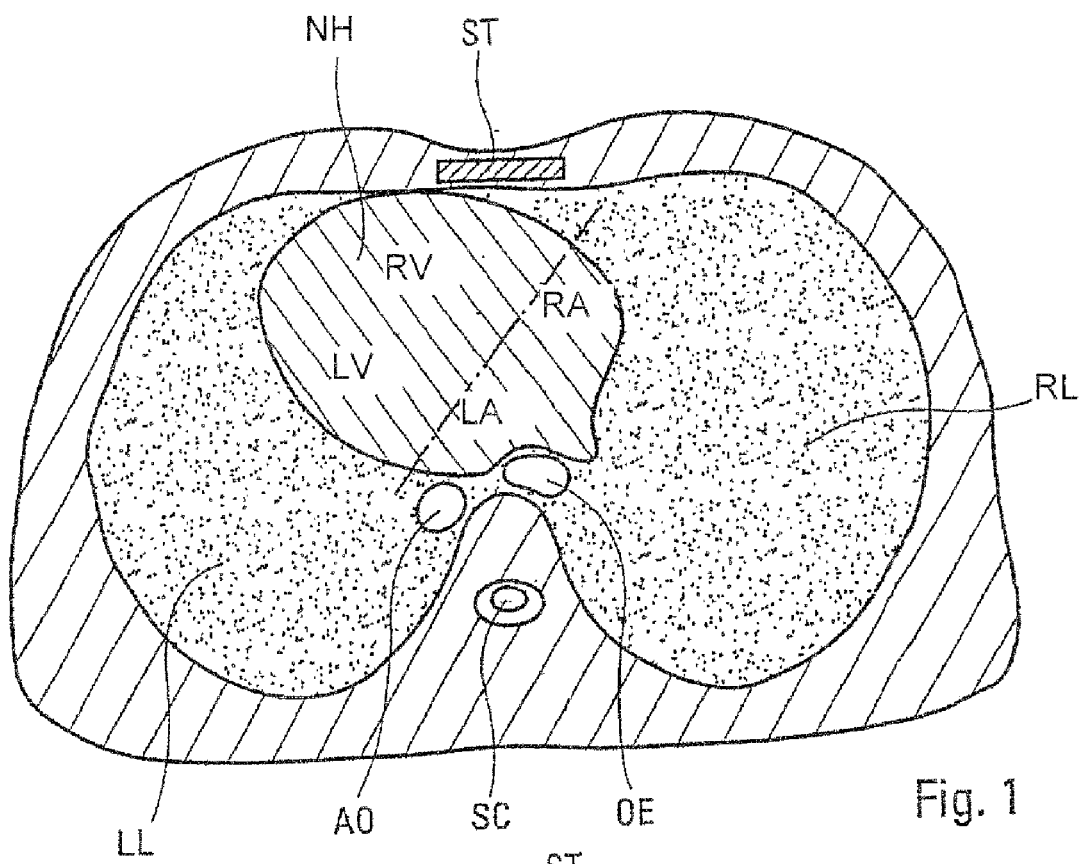
FIGS. 1 and 2 illustrate, in a schematic cross section through a patient's thorax, the process preparatory to the implantation of the heart prosthesis according to the invention.

The cross section of the thorax shown schematically in FIG. 1 depicts the left lung LL, the right lung RL, the sternum ST, the aorta AO, the spinal cord SC, the oesophagus OE and the natural heart NH of a patient. On this natural heart, the left auricle LA, the right auricle RA, the left ventricle LV and the right ventricle RV are depicted.

Figure 2:
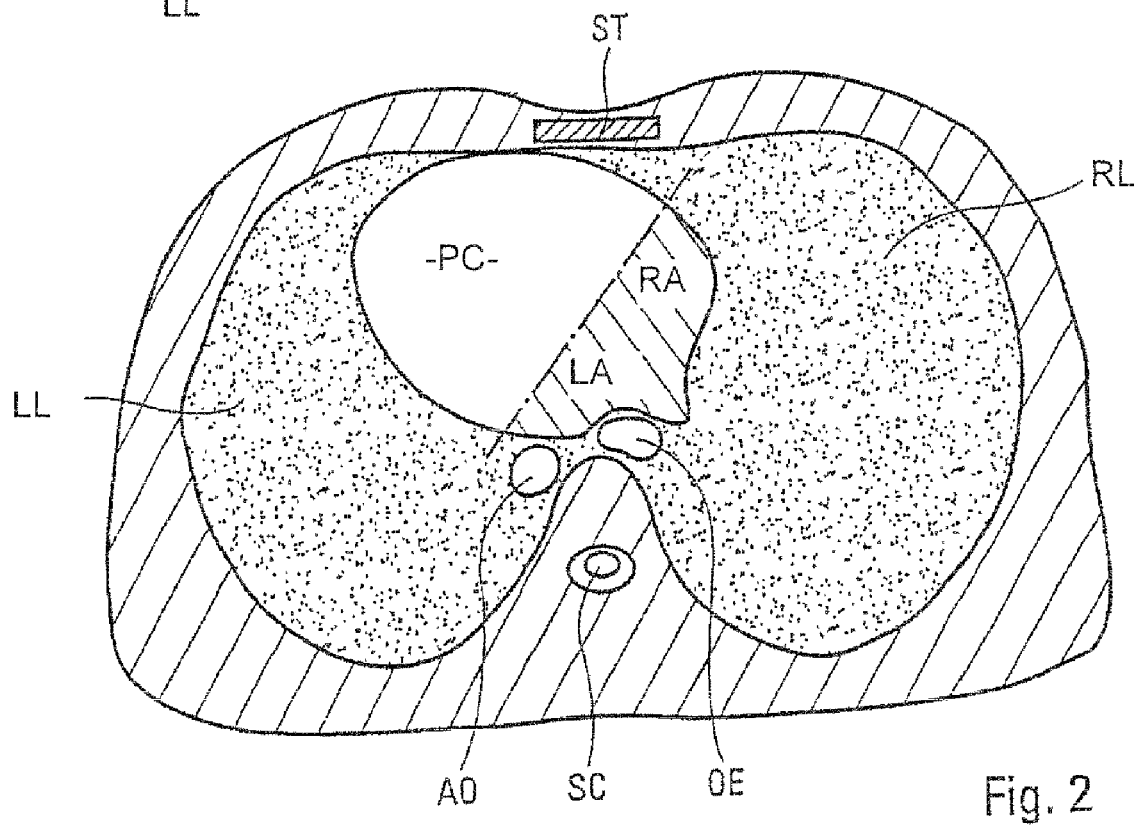
Figure 3:
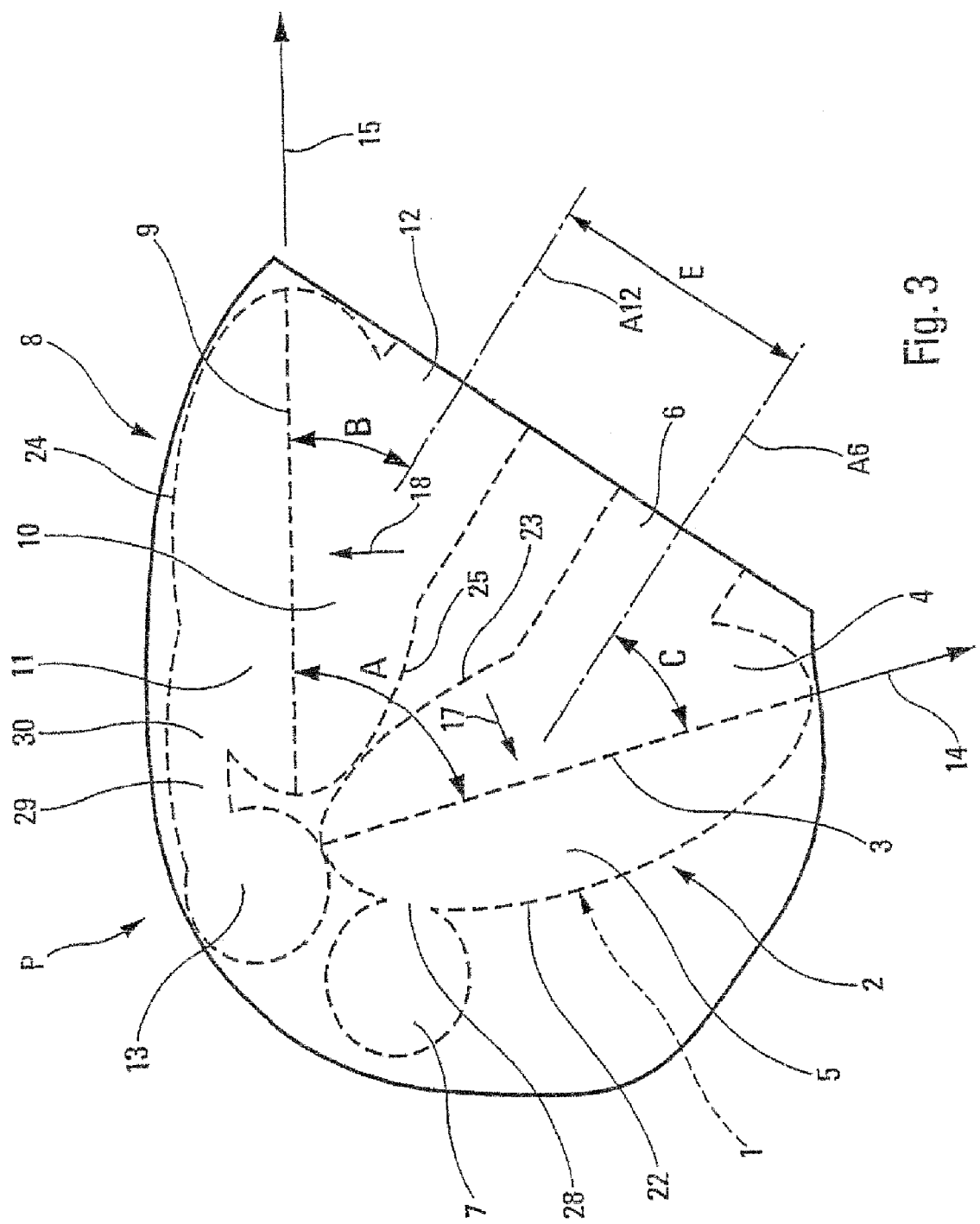
FIG. 3 shows a schematic representation of an illustrative embodiment of the heart prosthesis according to the invention.
Figure 4:
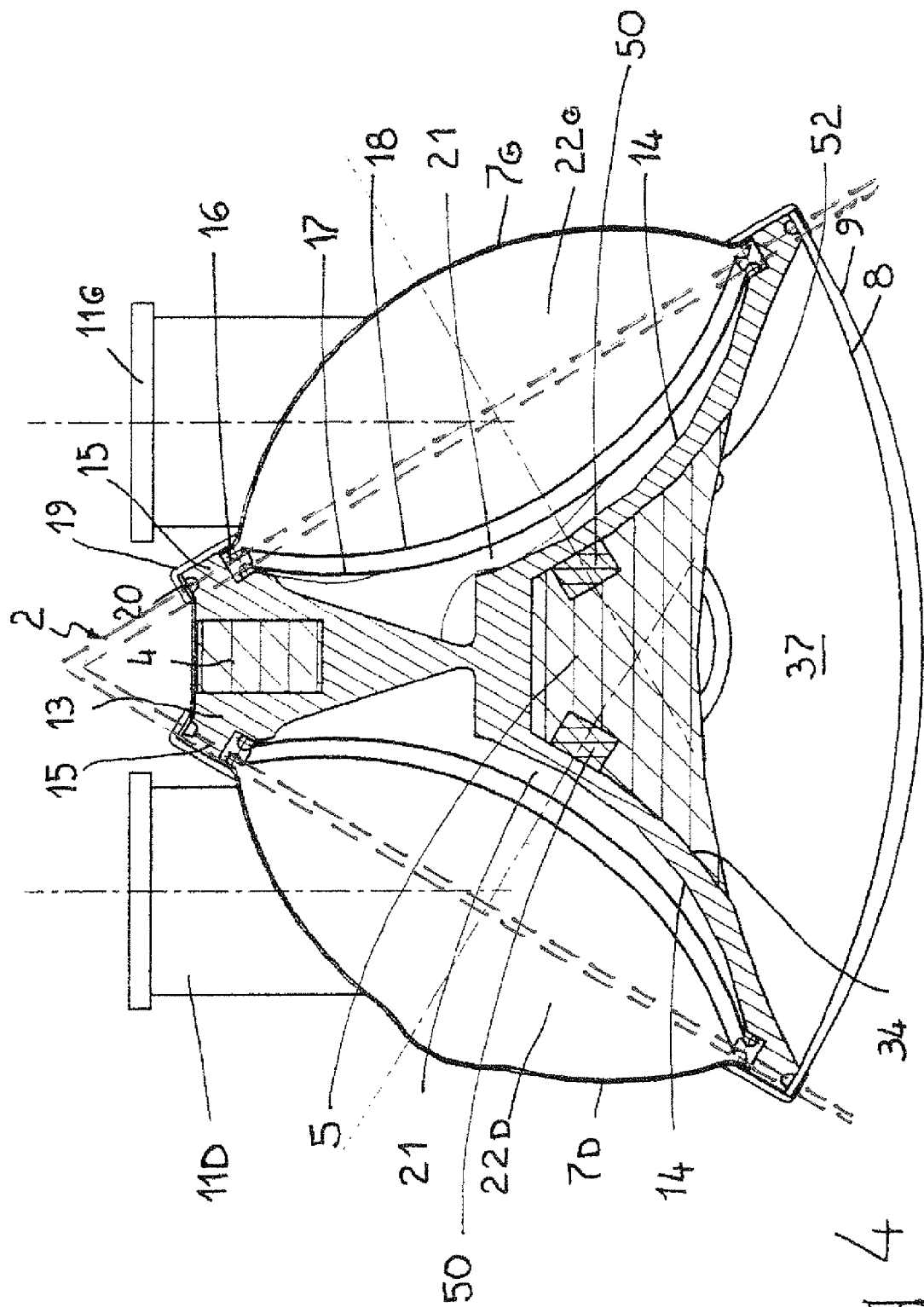
FIG. 4 illustrates, in a cross section similar to FIGS. 1 and 2, the implantation of the prosthesis from FIG. 3.
Figure 5:
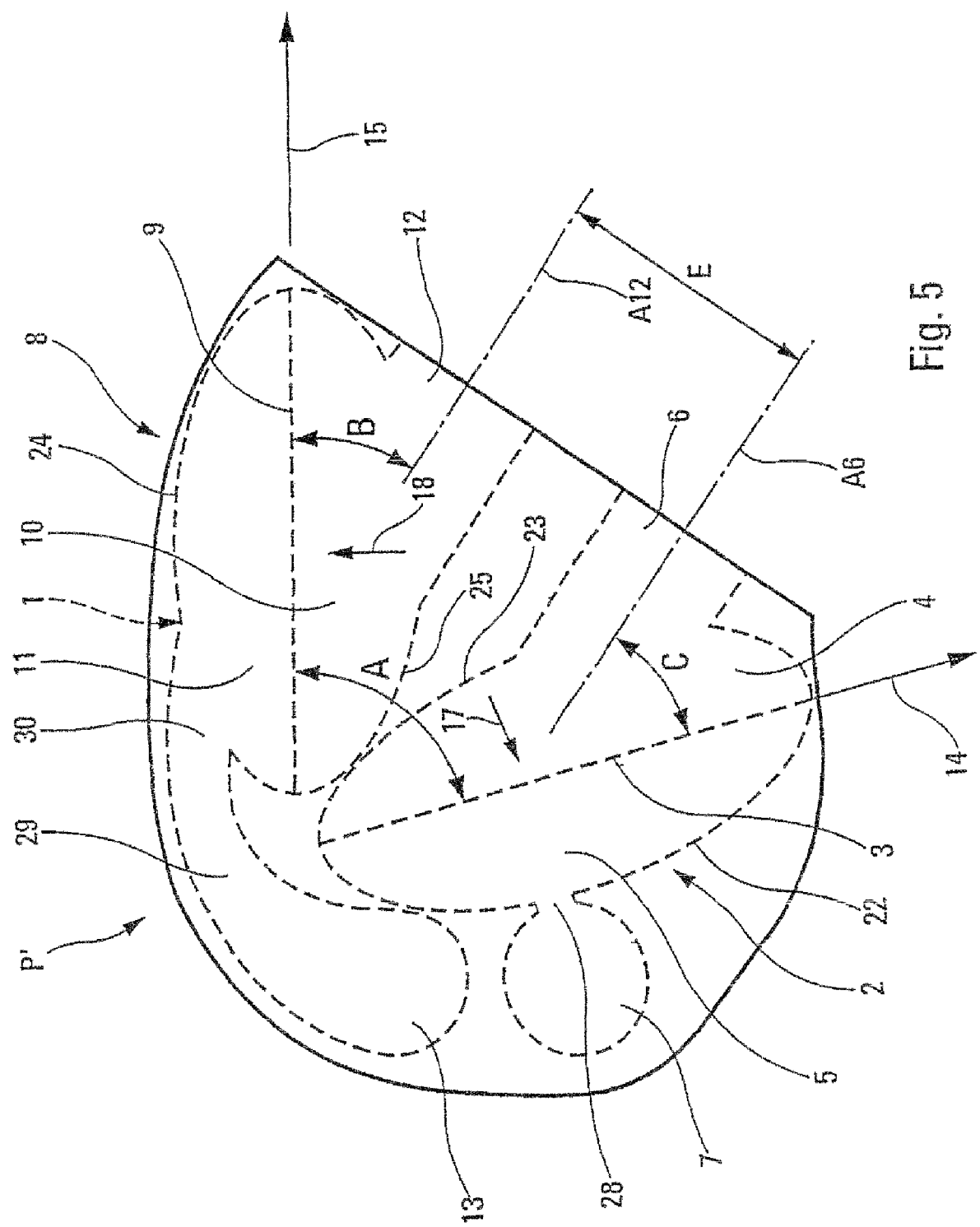
FIG. 5 illustrates, in a view similar to FIG. 3, an alternative embodiment of the heart prosthesis according to the present invention.

The heart prostheses P and P' according to the present invention, shown schematically and on an enlarged scale in FIGS. 3 and 5, respectively, are designed to replace the left and right ventricles LV and RV, after their removal, as is illustrated schematically in FIG. 2. To do this, the heart prostheses P and P' must be able to be lodged in the part of the pericardial cavity PC left free by the removal of said ventricles LV and RV (see FIGS. 2 and 4).

Figure 8:
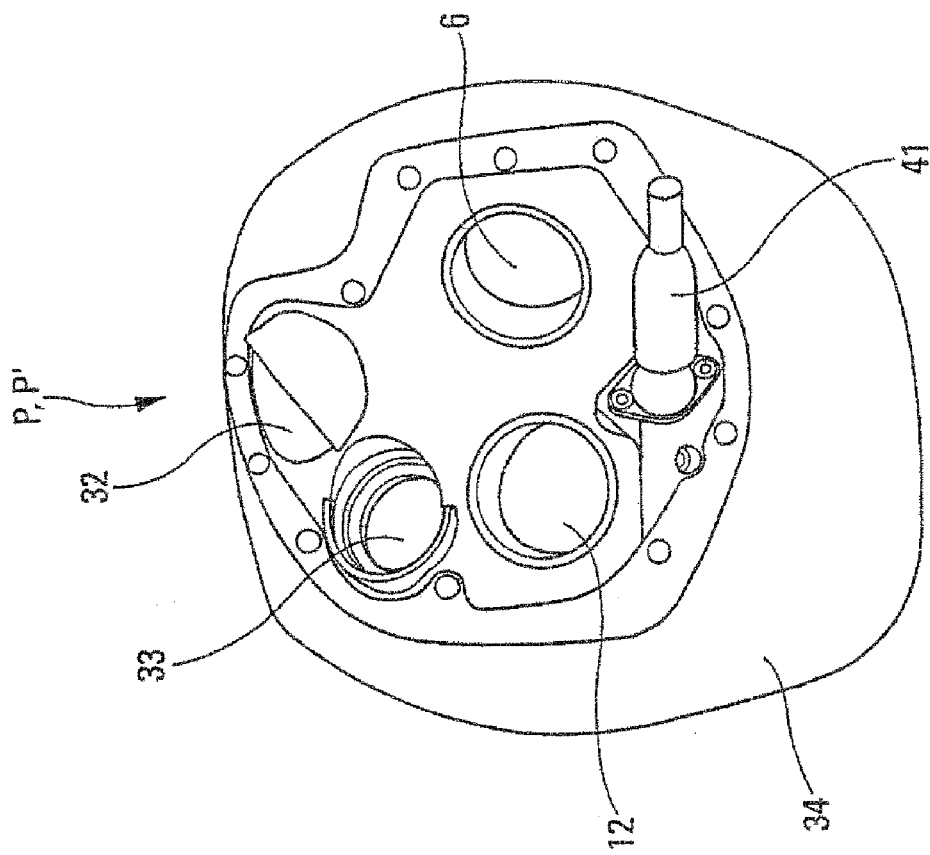
FIG. 8 is a plan view of the prosthesis according to the invention.
Figure 9:
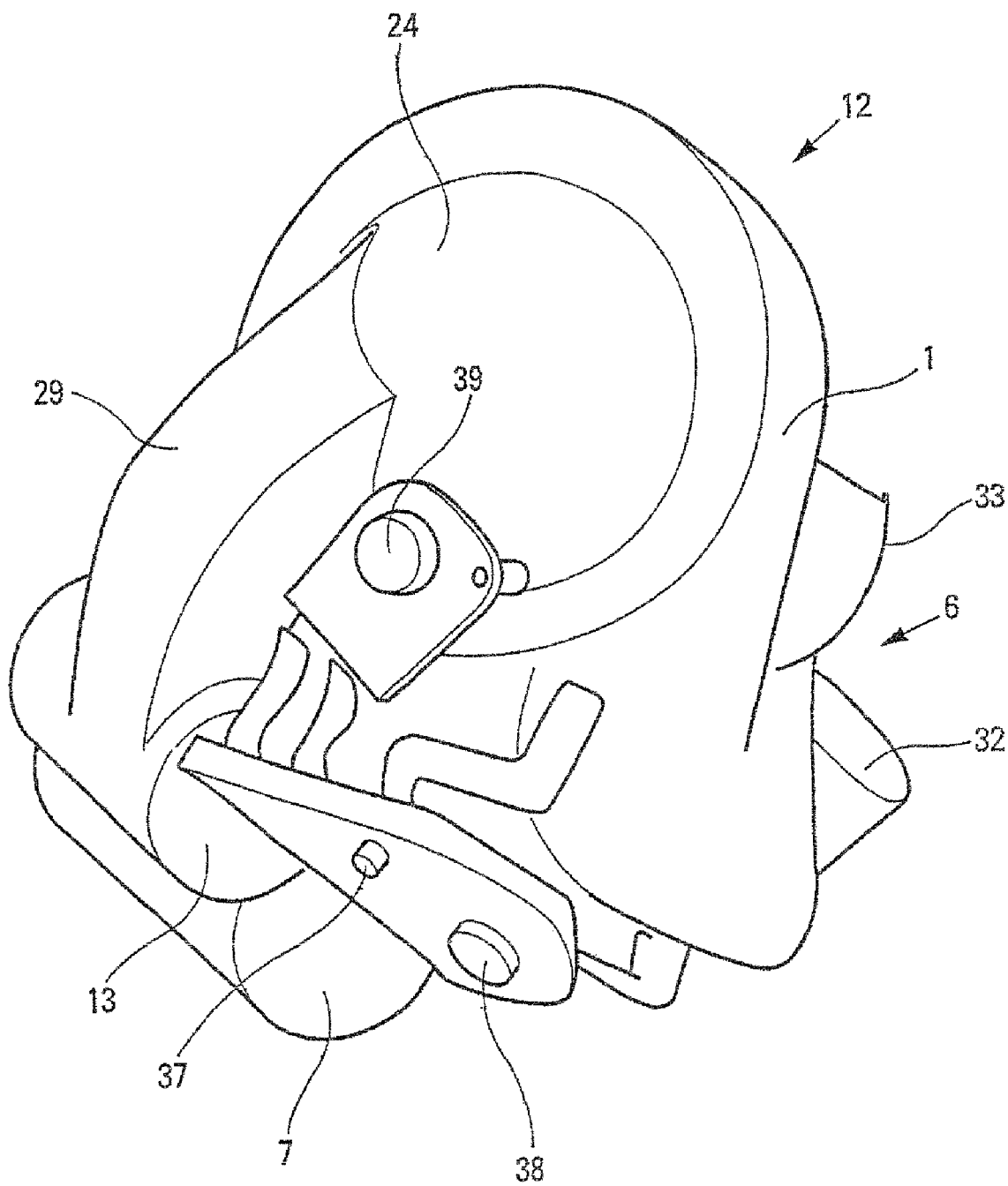
FIG. 9 is a perspective view of the prosthesis according to the invention, after removal of said leaktight flexible pouch and of the surrounding openworked wall.

As is shown schematically in FIGS. 3, 5 and 9, the heart prostheses P and P' comprise a rigid body 1, in which are arranged:

an artificial left ventricle 2 comprising a flexible membrane 3 which divides said artificial ventricle 2 in a leaktight manner into a chamber 4 for circulation of the blood and a chamber 5 for a hydraulic fluid, said blood chamber 4 comprising an orifice 6 of connection to the natural left auricle LA and means 33 of connection to the aorta AO (not shown in FIG. 3, but visible in FIG. 8);

a hydraulic actuator 7 for example of the motorized volumetric pump type, communicating with the hydraulic fluid chamber 5 of the artificial left ventricle 2 via a passage 28;

an artificial right ventricle 8, comprising a flexible membrane 9 which divides said artificial ventricle 8 in a leaktight manner into a chamber 10 for circulation of the blood and a chamber 11 for a hydraulic fluid, said blood chamber 10 comprising an orifice 12 of connection to the natural right auricle RA and means 32 of connection to the pulmonary artery (not shown in FIG. 3, but visible in FIG. 8); and a hydraulic actuator 13, for example also of the motorized volumetric pump type, communicating with the hydraulic fluid chamber 11 of the artificial right ventricle 8 via a passage 29.

The axis A6 of the connection orifice 6 and the axis A12 of the connection orifice 12 are at least approximately parallel, their distance E being at least approximately equal to 45 mm in the case where the heart prosthesis P is intended for an adult.

Moreover, as is also shown schematically in FIG. 3:

the respective general directions 14 and 15 of the artificial left ventricle 2 and artificial right ventricle 8, parallel to the plane of the axes A6 and A12, are convergent, forming between them an angle A, for example of the order of 80°, such that said ventricles are arranged in a V-shape and approach each other as they move away from the orifices 6 and 12 of connection to the left auricle LA and right auricle RA, respectively;

the V-shaped arrangement of the artificial left ventricle 2 and artificial right ventricle 8 is asymmetrical with respect to the axes A6 and A12, the angle B formed between the general direction 15 of the artificial right ventricle and the axis A12 of the orifice 12 of connection to the natural right auricle RA being greater than the angle C formed between the general direction 14 of the artificial left ventricle and the axis A6 of the orifice 6 of connection to the natural left auricle LA. In the above example where the angle A is equal to approximately 80°, the angles B and C can be approximately equal to 50° and 30°, respectively; and the individual hydraulic actuators 7 and 13 are arranged near each other, in proximity to the artificial left ventricle 2. In the embodiment P of the prosthesis according to the invention (FIG. 3), the individual hydraulic actuators 7 and 13 are arranged in proximity to the tip of the V.

By contrast, in the embodiment P' (FIG. 5), said individual hydraulic actuators 7 and 13 are at a distance from this tip.

Thus, compact prostheses P and P' are obtained that can be lodged in the pericardial cavity PC with the artificial right ventricle 11 parallel to the thorax and in line with the sternum, as is illustrated schematically in FIG. 4 for the prosthesis P. If appropriate, as is also shown in FIG. 4, the size of the prosthesis according to the invention can be slightly larger than the pericardial cavity PC (see broken line 16 delimiting the interior of the latter). In this case, it compresses the left lung LL only slightly.

Figure 6:
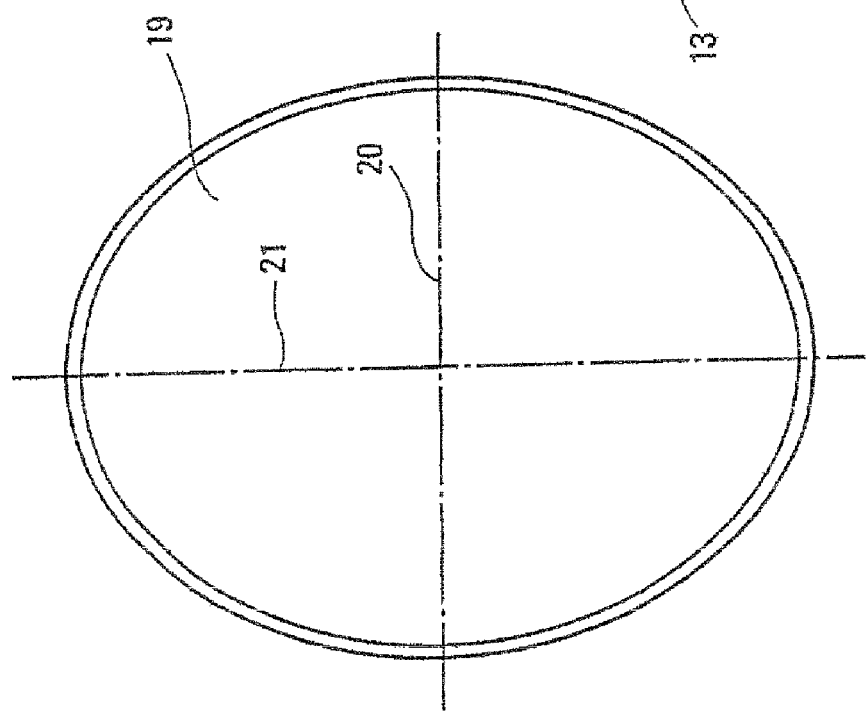
FIG. 6 illustrates the elliptic shape of the artificial ventricles of the prosthesis according to the present invention.

Furthermore, to optimize the size of the heart prostheses P and P' parallel to the antero-posterior axis of the thorax, it is advantageous that, seen in the plane of the arrows 17 and 18 in FIGS. 3 and 5, the artificial ventricles 2 and 8 have the shape of an ellipse 19 (see FIG. 6), of which the minor axis 20 is parallel to the general direction 14 or 15, and of which the major axis 21 is transverse with respect to the plane of FIG. 3. Each artificial ventricle 2 and 8 is formed by two opposite domes 22, 23 or 24, 25, respectively, which are connected to each other by a base 26, 27 with the shape of the ellipse 19, thus trapping the edge of the membrane 3 or 9. For an artificial ventricle 2 or 8 with a capacity of close to 70 $cm^3$, the minor axis 20, the major axis 21 and the distance d between the summits of two associated domes are at least approximately equal to 64 mm, 87 mm and 30 mm, respectively.

Figure 10:
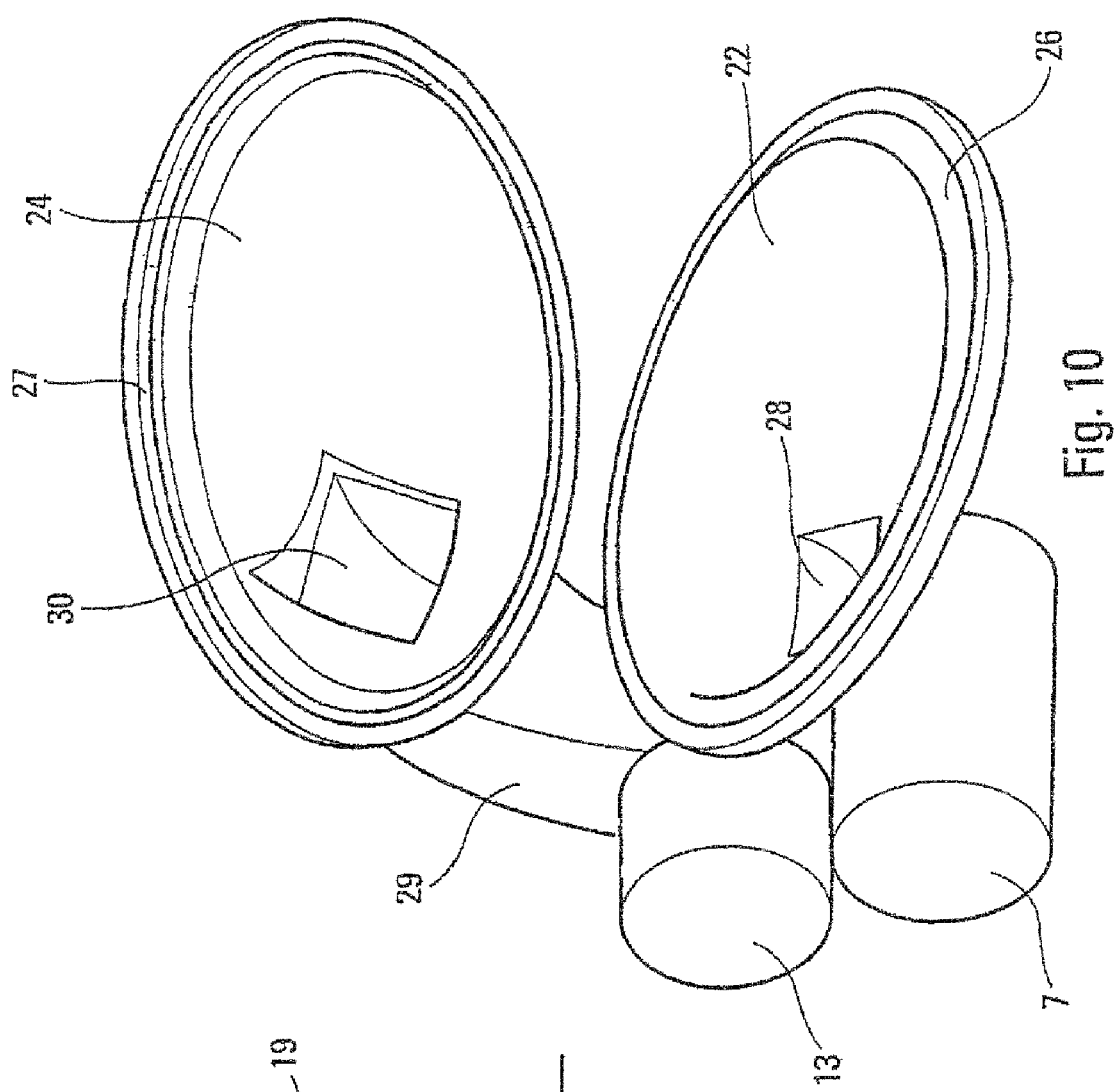
FIG. 10 is a perspective view showing the hydraulic actuators and the covers of the artificial ventricles.

Advantageously, the domes 23 and 25 corresponding respectively to the blood chambers 4 and 10 are formed by recesses made in the rigid body 1, while the domes 22 and 24, corresponding respectively to the hydraulic fluid chambers 5 and 11, are designed as covers that close off said artificial ventricles 2 and 8, respectively (see FIG. 10).

As the hydraulic actuator 7 is close to the artificial ventricle 2, its output can be connected to the latter by the short passage 28 extending through the dome 22. By contrast, as the hydraulic actuator 13 is set away from the artificial ventricle 8, its output is connected to the latter by the conduit 29 which is arranged outside of the body 1 and opens into the dome 24 by way of an opening 30 (see FIG. 10).

Figure 7:
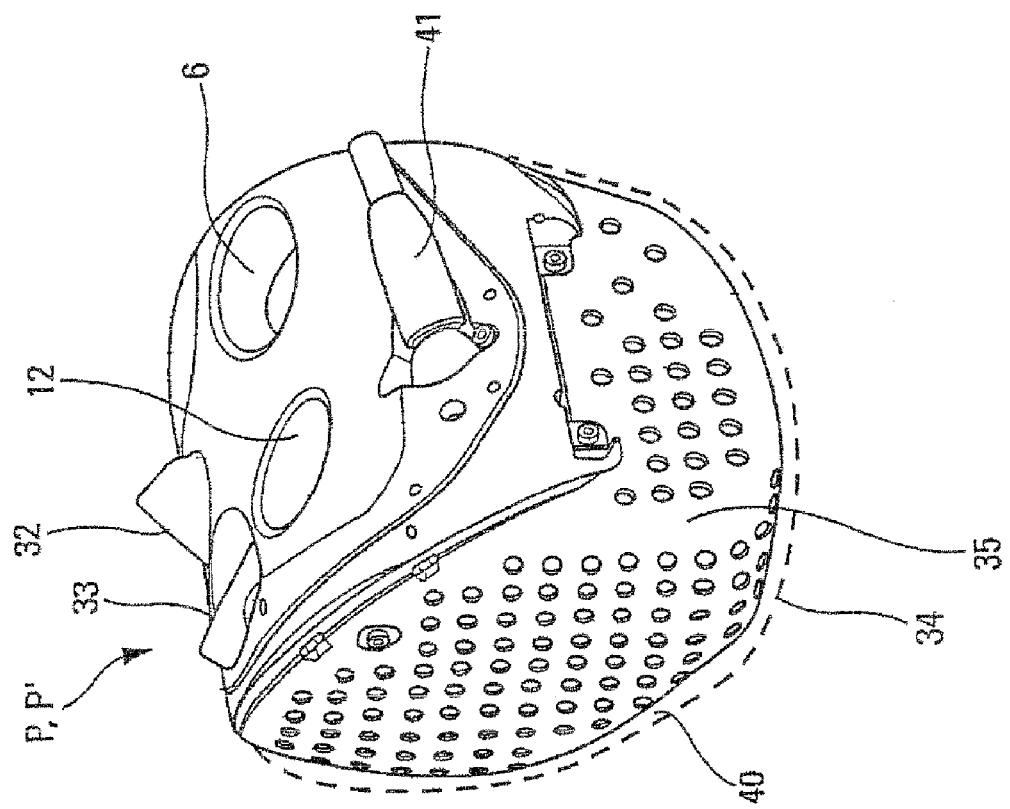
FIG. 7 is a perspective view of the prosthesis according to the invention, without its envelope formed by a leaktight flexible pouch.

As is shown in FIGS. 7 and 8, the heart prostheses P and P' are in the form of a volume of anatomical shape (corresponding to the shape of the pericardial cavity PC) provided with an orifice 6 of connection to the natural left auricle LA, with an orifice 12 of connection to the natural right auricle RA, means 33 of connection to the aorta AO and means 32 of connection to the pulmonary artery. Moreover, these figures show the base 41 of an electrical connection to the outside.

The body 1 of the heart prostheses P and P' is closed in a leaktight manner in a flexible pouch 34 amply surrounding said body and filled with the hydraulic fluid acted on by the actuators 7 and 13, which are immersed in this fluid. The flexible pouch 34 also serves as a container for this fluid.

Between the flexible pouch 34, on the one hand, and the body 1 and actuators 7 and 13, on the other hand, there is an openworked rigid wall 35 forming a strainer and allowing circulation of the hydraulic fluid inside the pouch 34. The openworked wall 35 avoids said flexible pouch being aspirated by the actuators 7 and 13.

A clearance volume 40 for said pouch 34 is formed between the openworked rigid wall 35 and the pouch 34. This clearance volume 40 is preferably at least approximately equal to twice the volume of a hydraulic fluid chamber 5, 11 of an artificial ventricle 2, 8.

FIG. 9 is a perspective view of an embodiment of the body 1, actuators 7 and 13 and passage 29 located inside the apertured surrounding wall 35 and the flexible pouch 34. In this figure, the orifices 6 and 12 of connection to the natural left and right auricles LA and RA are not visible, but their positions are indicated by arrows.

FIG. 9 also shows electronic control elements, such as a sensor 37 for the pressure inside the flexible pouch 34, a sensor 38 for the pressure in the artificial left ventricle 2 and a sensor 39 for the pressure in the artificial right ventricle 8. Thus, the heart prosthesis according to the present invention incorporates all the electronic elements for activation, control, processing, communication and regulation which are needed for its operation and which, as a result, are lodged in an anatomical position in the pericardial cavity.

The invention claimed is:

1. A heart prosthesis implantable in a pericardial cavity of a patient, said prosthesis being configured to replace natural left and right ventricles of said patient after their removal and comprising a rigid body in which artificial left and right ventricles are arranged, each of the artificial ventricles comprising a flexible membrane that is:

configured to beat under the action of a hydraulic fluid, and arranged in a cavity divided in a leaktight manner by said membrane into two chambers, one of which is intended for circulation of blood, and the other of which is filled with said hydraulic fluid, the hydraulic fluid chamber of each artificial ventricle being connected to an individual hydraulic actuator while the blood chamber of the artificial left ventricle comprises an orifice of connection to the natural left auricle and means of connection to the aorta, and the blood chamber of the artificial right ventricle comprises an orifice of connection to the natural right auricle and means of connection to the pulmonary artery, the axes of said orifices of connection to the natural auricles being co-planar, and said artificial ventricles having, parallel to the plane of said axes of said orifices general directions arranged in a V-shape, such that said ventricles approach each other as they move away from said orifices of connection to the natural auricles, wherein:

said axes of said orifices of connection to the natural auricles are at least approximately parallel;

said V-shaped arrangement of the artificial left and right ventricles is asymmetrical with respect to said axes, an angle formed between the general direction of the artificial right ventricle and the axis of said orifice of connection to the natural right auricle greater than the angle formed between the general direction of the artificial left ventricle and the axis of said orifice of connection to the natural left auricle; and said individual hydraulic actuators, associated respectively with said artificial left and right ventricles are arranged near each other, on the side of said artificial left ventricle.

2. The heart prosthesis according to claim 1, wherein the distance between said parallel axes of said connection orifices is at least approximately equal to 45 mm.

3. The heart prosthesis according to claim 1, wherein said individual hydraulic actuators are arranged in proximity to the tip of said V.

4. The heart prosthesis according to claim 1, wherein the dimensions of said artificial ventricles, parallel to said general directions thereof, are smaller than the dimensions of said ventricles perpendicular to said general directions.

5. The heart prosthesis according to claim 4, in which each of said artificial ventricles has the shape of two domes arranged opposite with respect to a common base, wherein said common base has the shape of an ellipse of which the minor axis is at least substantially parallel to said corresponding general direction of the ventricle.

6. The heart prosthesis according to claim 5 intended for an adult, wherein the lengths of the minor axis and of the major axis of said elliptic base are at least approximately equal to 64 mm and 87 mm, respectively.

7. The heart prosthesis according to claim 6, wherein the distance between the summits of the two domes is at least approximately equal to 30 mm.

8. The heart prosthesis according to claim 1, wherein the angle formed by said general directions of said artificial ventricles is at least approximately equal to 80°.

9. The heart prosthesis according to claim 8, wherein the angle formed between the general direction of the artificial right ventricle and the axis of said orifice of connection to the natural right auricle is at least approximately equal to 50°, and the angle formed between the general direction of the artificial left ventricle and the axis of said orifice of connection to the natural left auricle is at least approximately equal to 30°.

10. The heart prosthesis according to claim 1, wherein the individual hydraulic actuator associated with the artificial right ventricle is connected to the latter via a passage outside said rigid body.

11. The heart prosthesis according to claim 1, wherein it comprises:
- a flexible pouch surrounding, amply and sealingly, at least part of said rigid body by enclosing said hydraulic actuators and the electronics for control, signal processing and communication, said pouch being filled with said hydraulic fluid and serving as a container for the hydraulic circuit of said actuators; and
- a surrounding openworked and rigid wall which is integral with said rigid body and which is arranged between the latter and said flexible pouch.

12. The heart prosthesis according to claim 11, wherein a clearance volume for said flexible pouch is formed between it and said openworked rigid wall.

13. The heart prosthesis according to claim 12, wherein said clearance volume is at least approximately equal to twice the volume of the hydraulic fluid chamber of one of said artificial ventricles and is distributed across the full surface of the rigid wall.

* * * * *